(12) United States Patent
Hasegawa et al.

(10) Patent No.: US 9,857,282 B2
(45) Date of Patent: Jan. 2, 2018

(54) PARTICLE ANALYZING APPARATUS

(71) Applicant: FUJI ELECTRIC CO., LTD., Kanagawa (JP)

(72) Inventors: Yoshiki Hasegawa, Hino (JP); Naoki Takeda, Yokohama (JP); Kazuhiro Koizumi, Sagamihara (JP); Takamasa Asano, Hino (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 0 days.

(21) Appl. No.: 15/364,266

(22) Filed: Nov. 30, 2016

(65) Prior Publication Data

US 2017/0212030 A1   Jul. 27, 2017

(30) Foreign Application Priority Data

Jan. 27, 2016  (JP) ................................ 2016-013697

(51) Int. Cl.
*G01N 21/00* (2006.01)
*G01N 15/06* (2006.01)
(Continued)

(52) U.S. Cl.
CPC ............. *G01N 15/06* (2013.01); *G01N 15/10* (2013.01); *G01N 21/05* (2013.01); *G01N 21/53* (2013.01); *G01N 2001/2255* (2013.01); *G01N 2001/2264* (2013.01); *G01N 2015/0693* (2013.01); *G01N 2021/1734* (2013.01); *G01N 2021/1761* (2013.01)

(58) Field of Classification Search
CPC ....... G01N 15/1459; G01N 2015/1486; G01N 2001/2223; G01N 2001/2264; G01N 2001/2255
See application file for complete search history.

(56) References Cited

U.S. PATENT DOCUMENTS 4,828,660 A * 5/1989 Clark ........................ B01D 1/02
                                                          134/109
2007/0251307 A1* 11/2007 Graze, Jr. ............ G01N 1/2252
                                                           73/114.69

(Continued)

FOREIGN PATENT DOCUMENTS

JP         S61-14543 A       1/1986
JP       2012-189483 A      10/2012

*Primary Examiner* — Michael A Lyons
*Assistant Examiner* — Maurice Smith (57) ABSTRACT

A particle analyzing apparatus including a particle measuring section that measures a number or concentration of particles in a sample gas; a component analyzing section that measures an amount of each component of the particles in the sample gas; a flow path that branches into a first flow path that introduces the sample gas to the particle measuring section and a second flow path that introduces the sample gas to the component analyzing section; a first adjusting section that is provided in the first flow path and dilutes the sample gas with a dilution gas and introduces the diluted sample gas to the particle measuring section to adjust a measurement range of the particle measuring section; and a second adjusting section that is provided in the second flow path and adjusts an introduction time during which the sample gas is introduced to the component analyzing section.

9 Claims, 6 Drawing Sheets

(51) Int. Cl.
 G01N 21/53 (2006.01)
 G01N 21/05 (2006.01)
 G01N 15/10 (2006.01)
 G01N 21/17 (2006.01)
 G01N 1/22 (2006.01)

(56) References Cited

U.S. PATENT DOCUMENTS

| | | | | |
|---|---|---|---|---|
| 2010/0000339 | A1* | 1/2010 | Silvis | G01N 1/2252 |
| | | | | 73/863.01 |
| 2012/0001067 | A1* | 1/2012 | Orii | G01N 15/0266 |
| | | | | 250/288 |
| 2012/0090377 | A1* | 4/2012 | Matsuyama | G01N 1/2252 |
| | | | | 73/23.33 |
| 2013/0011930 | A1 | 1/2013 | Takegawa et al. | |
| 2013/0133440 | A1* | 5/2013 | Wei | G01N 1/2252 |
| | | | | 73/863.03 |
| 2016/0061798 | A1* | 3/2016 | Wapelhorst | G01N 33/0011 |
| | | | | 73/23.2 |
| 2016/0319726 | A1* | 11/2016 | Otsuki | G01N 1/2252 |

* cited by examiner

PARTICLE ANALYZING APPARATUS

BACKGROUND

The contents of the following Japanese patent application are incorporated herein by reference:
NO. 2016-013697 filed on Jan. 27, 2016.

1. Technical Field

The present invention relates to a particle analyzing apparatus.

2. Related Art

There has been interest in technology for measuring particles such as $PM_{2.5}$ in the air. A conventional particle measuring apparatus is known that measures the number and size of particles based on laser light scattered by the particles in sample air, as shown in Patent Document 1, for example. Furthermore, a component analyzing apparatus is known that analyzes the amount of each component of the particles in a sample gas, as shown in Patent Document 2, for example. Yet further, a measuring apparatus is known that dilutes exhaust gas with dilution air, in order to expand the measurement range according to the concentration of the exhaust gas when measuring exhaust gas containing a high concentration of particles, as shown in Patent Document 3, for example. In this measuring apparatus, a portion of the diluted exhaust gas is guided to the measuring apparatus and the number of particles contained in this gas is counted.

Patent Document 1: Japanese Patent Application Publication No. 2012-189483
Patent Document 2: International Publication WO 2011/114587
Patent Document 3: International Publication WO 2010/116959

In order to perform multiple types of analyses on the target particles, there is an idea of using a composite particle analyzing apparatus that includes both a particle measuring section and a component analyzing section. However, when uniformly diluting the sample gas and performing measurement with the particle measuring section and the component analyzing section, there are cases where the detection sensitivity of one of the particle measuring section and the component analyzing section is reduced. Accordingly, there have been cases where it is difficult to expand the measurement range while preventing a decrease in the detection sensitivity in the particle analyzing apparatus including the particle measuring section and the component analyzing section.

SUMMARY

According to a first aspect of the present invention, provided is a particle analyzing apparatus. The particle analyzing apparatus may comprise a particle measuring section, a component analyzing section, a flow path, a first adjusting section, and a second adjusting section. The particle measuring section may measure a number or concentration of particles in a sample gas, based on laser light that is scattered by the particles in the sample gas. The component analyzing section may measure an amount of each component of the particles in the sample gas. The flow path may have one end thereof connected to the sample gas source. The flow path may branch into a first flow path and a second flow path, at a branching point at the other end side. The first flow path may introduce the sample gas to the particle measuring section. The second flow path may introduce the sample gas to the component analyzing section. The first adjusting section may be provided in the first flow path. The first adjusting section may dilute the sample gas with a dilution gas. The first adjusting section may introduce the diluted sample gas to the particle measuring section to adjust a measurement range of the particle measuring section. The second adjusting section may be provided in the second flow path. The second adjusting section may adjust an introduction time during which the sample gas is introduced to the component analyzing section.

The first adjusting section may include a dilution gas flow path and a dilution gas flow rate control section. The dilution gas flow path may have one end thereof connected to a dilution gas source. The dilution gas flow path may have another end thereof connected to the first flow path. The dilution gas flow rate control section may be provided in the dilution gas flow path. The dilution gas flow rate control section may control a flow rate of the dilution gas introduced to the first flow path.

The particle analyzing apparatus may comprise an exhaust gas flow rate control section. The exhaust gas flow rate control section may control a flow rate of an exhaust gas emitted from the particle measuring section The particle analyzing apparatus may comprise a dilution rate calculating section and a concentration calculating section. The dilution rate calculating section may calculate a dilution rate based on the flow rate of the dilution gas in the dilution gas flow rate control section and the flow rate of the exhaust gas in the exhaust gas flow rate control section. The concentration calculating section may calculate a concentration of particles in the sample gas that has not been diluted, based on the dilution rate and the measurement result of the particle measuring section.

The second adjusting section may include a sample gas flow rate control section and a flow path opening/closing section. The sample gas flow rate control section may be arranged in the second flow path. The sample gas flow rate control section may control a flow rate of the sample gas. The flow path opening/closing section may be arranged in the second flow path. The flow path opening/closing section may adjust an introduction time during which the sample gas is introduced into the component analyzing section by switching between an open state and a closed state.

The particle analyzing apparatus may comprise an introduction amount calculating section. The introduction amount calculating section may calculate an introduction amount of the sample gas into the component analyzing section based on the flow rate of the sample gas in the sample gas flow rate control section and the introduction time during which the sample gas is introduced into the component analyzing section as adjusted by the flow path opening/closing section. The second adjusting section may control the introduction rate of the sample gas to be within a predetermined range by adjusting a time of the open state of the flow path opening/closing section.

The component analyzing section may include a particle beam generating section, a trap, an energy beam emitting section, and an analyzer. The particle beam generating section may emit a particle beam formed by particles in the sample gas. The trap that may be arranged at a position at which the particle beam is emitted. The trap may trap the particles in the particle beam. The energy beam emitting section may irradiate the trap with an energy beam to create a desorbed component by vaporizing, sublimating, or causing a reaction with the particles trapped in the trap. The analyzer may measure an amount of each component of the particles by analyzing the desorbed component.

The particle analyzing apparatus may comprise a bypass flow path, a bypass flow rate control section, and an exhaust gas flow path. The bypass flow path may branch from the second flow path. The bypass flow rate control section may be provided in the bypass flow path. The bypass flow rate control section may control a flow rate of the sample gas flowing through the bypass flow path such that a necessary flow rate of the sample gas introduced into the entire particle analyzing apparatus from the sample gas source is within a predetermined range. The exhaust gas flow path may have exhaust gas emitted from the particle measuring section flow therethrough. The bypass flow path may be connected to the exhaust gas flow path.

The introduction time of the sample gas may be shorter when the number or concentration of the particles measured by the particle measuring section is higher.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
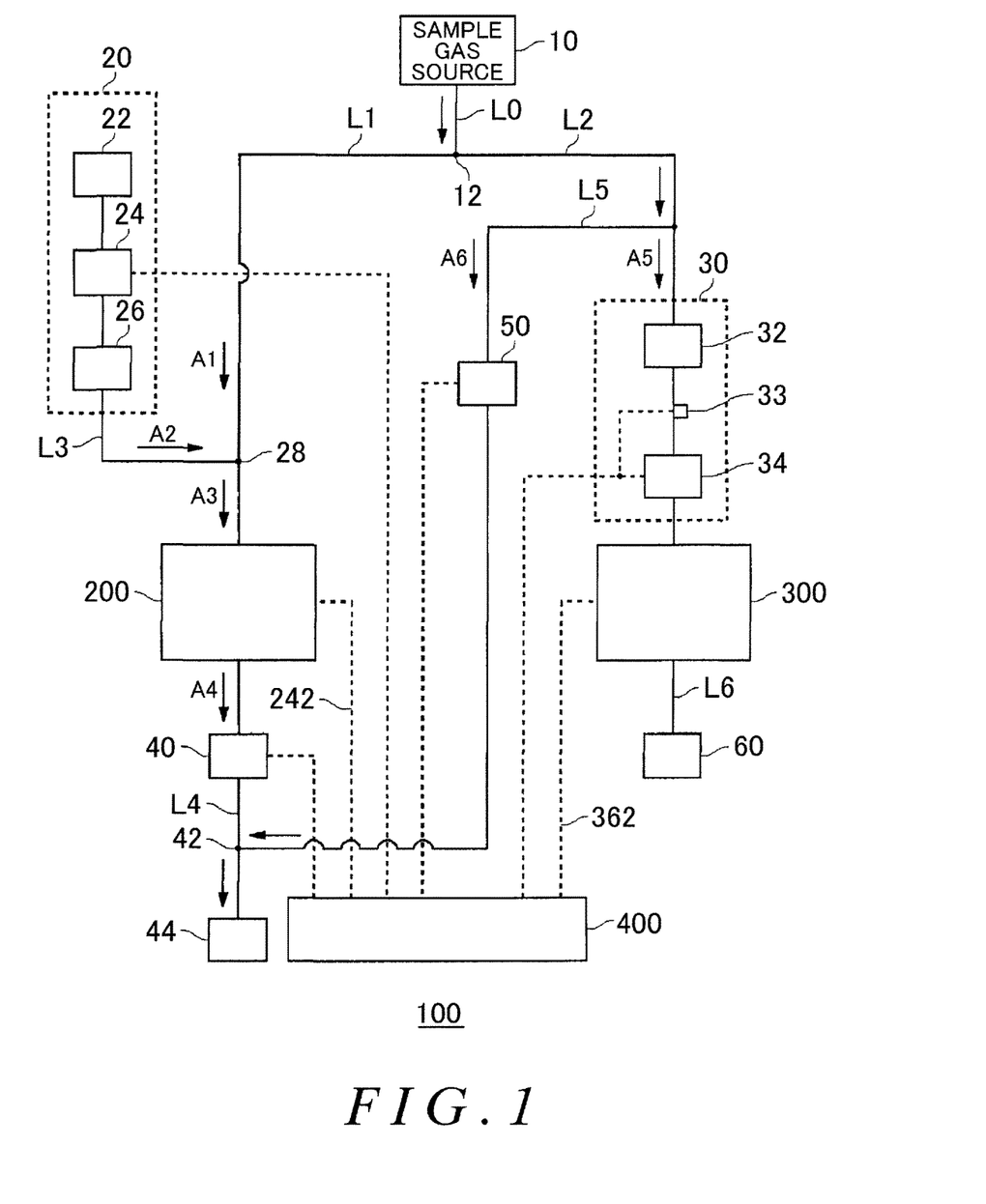
FIG. 1 shows the overall configuration of a particle analyzing apparatus 100 according to an embodiment of the present invention.

FIG. 1 shows the overall configuration of a particle analyzing apparatus 100 according to an embodiment of the present invention. The particle analyzing apparatus 100 includes a particle measuring section 200, a component analyzing section 300, and a processing section 400. The particle measuring section 200 measures the number or concentration of particles in a sample gas. The particle measuring section 200 may further measure the size of the particles. The component analyzing section 300 may measure the amount of each component of the particles in the sample gas. For example, the component analyzing section 300 measures the mass of each chemical component of the particles. The sample gas may be air, or may be exhaust from an automobile or the like.

The particle analyzing apparatus 100 in this example includes the particle measuring section 200 and the component analyzing section 300 having measurement mechanisms that differ from each other. The particle analyzing apparatus 100 may be a composite analyzing apparatus that performs multiple types of analyses on aerosol, which is particles floating in the sample gas. The particle measuring section 200 and the component analyzing section 300 may be arranged in respective casings, and may each perform processes independently.

The particle measuring section 200 and the component analyzing section 300 are connected in parallel. The particle analyzing apparatus 100 includes a gas flow path that branches into a first flow path L1 and a second flow path L2. The first flow path L1 introduces the sample gas into the particle measuring section 200. The second flow path L2 introduces the sample gas into the component analyzing section 300.

The particle analyzing apparatus 100 in this example includes a flow path L0 that is an introduction pipe. One end of the flow path L0 is connected to a sample gas source 10. The sample gas source 10 may be a sample gas entrance for air or exhaust serving as the measurement target. The other end side of the flow path L0 branches into the first flow path L1 and the second flow path L2 at a branching point 12. The first flow path L1 and the second flow path L2 may also be pipes.

The particle analyzing apparatus 100 may have the first flow path L1 and the second flow path L2 directly connected to the sample gas source 10, without including the flow path L0. In either example, sample gas is introduced into the first flow path L1 and the second flow path L2 with the same concertation.

The particle analyzing apparatus 100 includes a first adjusting section 20 and a second adjusting section 30. The first adjusting section 20 is provided in the first flow path L1. The first adjusting section 20 dilutes the sample gas with a dilution gas and introduces the resulting gas to the particle measuring section 200. The first adjusting section 20 adjusts the measurement range of the particle measuring section 200 by introducing the diluted sample gas to the particle measuring section 200.

The first adjusting section 20 may include a dilution gas flow path L3, a dilution gas source 22, a dilution gas flow rate control section 24, and a cleaning section 26. One end of the dilution gas flow path L3 is connected to the dilution gas source 22 via the dilution gas flow rate control section 24 and the cleaning section 26. The other end of the dilution gas flow path L3 is connected to the first flow path L1 at a merging point 28. The dilution gas flow path L3 may include a plurality of pipes for providing connections between the dilution gas source 22 and the dilution gas flow rate control section 24, between the dilution gas flow rate control section 24 and the cleaning section 26, and between the cleaning section 26 and the merging point 28. The merging point 28 may be a branched pipe that connects the dilution gas flow path L3 to the first flow path L1, and may be a container that includes space for the dilution.

The dilution gas is clean dilution air that does not include any more than a predetermined amount of particles, for example. The dilution gas source 22 is a compressed air source, for example. The compressed air source may be a compressor. The sample gas from the sample gas source 10 and the dilution gas from the dilution gas source 22 are mixed together at the merging point 28. Accordingly, sample gas that has been diluted by the dilution gas flows downstream of the merging point 28. The sample gas diluted by the dilution gas is introduced to the particle measuring section 200. The dilution gas flow rate control section 24 is provided in the dilution gas flow path L3.

The dilution gas flow rate control section 24 measures the flow rate A2 of the dilution gas introduced to the first flow path L1, and controls this flow rate A2. The dilution gas flow rate control section 24 may include a flow rate sensor, a flow rate control valve, and a control circuit. Specifically, the dilution gas flow rate control section 24 may be a mass flow controller or a flowmeter with a needle valve. Flow rate setting values are input to the dilution gas flow rate control section 24 via the control circuit. The dilution gas flow rate control section 24 may measure the actual flow rate A2. The dilution gas flow rate control section 24 may continuously adjust the opening amount of the flow rate control valve such that the actual measurement value of the flow rate is controlled to be the flow rate setting value.

The cleaning section 26 includes a filter for cleaning the dilution gas by removing particles in the dilution gas. In this example, the cleaning section 26 is arranged downstream from the dilution gas flow rate control section 24, but in another example, the cleaning section 26 may instead be arranged upstream from the dilution gas flow rate control section 24. By removing the particles in the dilution gas, it is possible to prevent measurement errors caused by particles in the dilution gas. If the dilution gas supplied by the dilution gas source 22 is already clean to a point greater than or equal to a predetermined reference level, the cleaning section 26 may be omitted.

The particle analyzing apparatus 100 includes an exhaust gas flow path L4, an exhaust gas flow rate control section 40, and a first vacuum section 44. One end of the exhaust gas flow path L4 is connected to the exhaust outlet of the particle measuring section 200. The other end of the exhaust gas flow path L4 is connected to the first vacuum section 44. The first vacuum section 44 sucks in the exhaust gas via the exhaust gas flow path L4 and emits the exhaust gas to the outside of the system. The first vacuum section 44 may be a vacuum pump. The exhaust gas emitted from the particle measuring section 200 flows through the exhaust gas flow path L4. The exhaust gas is gas that has been measured by the particle measuring section 200. The particle measuring section 200 in this example emits the sample gas that has been diluted at the merging point 28 as exhaust gas after this sample gas has been measured.

The exhaust gas flow rate control section 40 is provided in the exhaust gas flow path L4. The exhaust gas flow rate control section 40 controls the flow rate A4 of the exhaust gas emitted from the particle measuring section 200. The exhaust gas flow rate control section 40 may have the same configuration as the dilution gas flow rate control section 24, aside from the control target gas being the exhaust gas instead of the dilution gas. The exhaust gas flow rate control section 40 may have the flow rate setting values input thereto. The exhaust gas flow rate control section 40 may measure the flow rate A4 of the exhaust gas.

In the particle analyzing apparatus 100 of this example, the measurement range of the particle measuring section 200 is adjusted by introducing the diluted sample gas. On the other hand, the sample gas diluted by the first adjusting section 20 is not introduced to the component analyzing section 300. The component analyzing section 300 is provided with a second adjusting section 30 that increases the measurement range using a different method than the first adjusting section 20.

The second adjusting section 30 is arranged in the second flow path L2. The second adjusting section 30 adjusts the introduction time during which the sample gas is introduced to the component analyzing section 300. The second adjusting section 30 may include a sample gas flow rate control section 32 and a flow path opening/closing section 34. The sample gas flow rate control section 32 is arranged in the second flow path L2. The sample gas flow rate control section 32 controls the flow rate A5 per unit time of the sample gas. The sample gas flow rate control section 32 is an orifice that is a throttle valve for controlling the flow rate A5 per unit time to become the setting value, for example.

If a control section that does not include a drive source, such as an orifice, is used as the sample gas flow rate control section 32, a pressure measuring section 33 may be arranged directly after the orifice. The pressure measuring section 33 may be a pressure meter such as a diaphragm that detects a pressure difference between the front and back of the orifice. An instruction value provided by the pressure measuring section 33 is electrically read and converted into the flow rate A5 per unit time of the sample gas for the sample gas flow rate control section 32.

The flow path opening/closing section 34 is arranged in the second flow path L2. The component analyzing section 300 is provided downstream from the flow path opening/closing section 34. In this example, the sample gas flow rate control section 32 is provided upstream from the flow path opening/closing section 34. It should be noted that the sample gas flow rate control section 32 may be provided downstream from the flow path opening/closing section 34, and that the flow path opening/closing section 34 may further include the function of the sample gas flow rate control section 32. A second vacuum section 60 is connected to an exhaust outlet of the component analyzing section 300 via an exhaust gas flow path L6. The second vacuum section 60 sucks in the exhaust gas via the exhaust gas flow path L6 from the component analyzing section 300 and emits this exhaust gas to the outside of the system. The second vacuum section 60 is a vacuum pump.

The flow path opening/closing section 34 switches between an open state and a closed state to adjust the introduction time during which the sample gas is introduced to the component analyzing section 300. When the flow path opening/closing section 34 controls the second flow path L2 to be in the closed state, the sample gas is not introduced to the component analyzing section 300, and when the flow path opening/closing section 34 controls the second flow path L2 to be in the open state, the sample gas is introduced to the component analyzing section 300. The flow path opening/closing section 34 may be an electrically-driven valve, e.g. a ball valve electrically driven by an actuator. However, the flow path opening/closing section 34 is not particularly limited to this, and any component may be used that is capable of controlling whether the sample gas is introduced to the component analyzing section 300.

The particle analyzing apparatus 100 includes a bypass flow path L5 that branches from the second flow path L2, and a bypass flow rate control section 50. One end of the bypass flow path L5 is connected to the second flow path L2. The other end of the bypass flow path L5 is connected to the exhaust gas flow path L4 via the bypass flow rate control section 50. A bypass merging point 42 connecting the bypass flow path L5 and the exhaust gas flow path L4 may be downstream from the exhaust gas flow rate control section 40. In this way, the actual measurement value of the flow rate A4 for the exhaust gas flow rate control section 40 is not affected.

The sample gas flowing through the bypass flow path L5 and the exhaust gas flowing through the exhaust gas flow path L4 are mixed together and emitted together to the outside of the system by the first vacuum section 44. Since the first vacuum section 44 is provided in common for the bypass flow path L5 and the exhaust gas flow path L4, there is no need to attach a vacuum section for each flow path, and therefore space can be saved.

The bypass flow rate control section 50 is provided in the bypass flow path L5. The bypass flow rate control section 50 controls the flow rate A6 of the sample gas flowing through the bypass flow path L5. The bypass flow rate control section 50 may be a mass flow controller or a flow meter with a needle valve. The bypass flow rate control section 50 may have the same configuration as the dilution gas flow rate control section 24 and the exhaust gas flow rate control section 40, aside from the control target gas being the gas flowing through the bypass flow path L5 instead of the dilution gas or the exhaust gas. Accordingly, a detailed description of this configuration is omitted.

The bypass flow rate control section 50 reduces the loss of sample microparticles in a case where the flow rate A1 of the sample gas introduced into the first flow path L1 from the sample gas source 10 and the flow rate A2 of the dilution gas are very low flow rates. For example, if the flow rate A1 and the flow rate A2 are each less than or equal to 10 mL/min, when the sample microparticles serving as the measurement target are sucked in to the particle measuring section 200 or the component analyzing section 300 from the sample gas source 10, there may be a large amount of pressure loss due to the tube diameter and tube length of the pipes L0, L1, and L2, and this may cause loss of the sample microparticles. However, in this example, the bypass flow rate control section 50 controls the sample gas to be sucked into the bypass flow path L5 with a flow rate greater than the flow rate A1 and the flow rate A2. Accordingly, it is possible to reduce the loss of sample microparticles.

The bypass flow rate control section 50 may perform control such that the necessary flow rate of sample gas flowing into the entire particle analyzing apparatus 100 from the sample gas source 10 is within a predetermined range. For example, the bypass flow rate control section 50 performs control such that the sum of the flow rates A1, A5, and A6 is always a constant amount, in order to keep the necessary flow rate of the sample gas at a constant amount for the entire particle analyzing apparatus 100.

As an example, the flow rate A1 can be changed as a result of the dilution gas flow rate control section 24 and the exhaust gas flow rate control section 40 adjusting the flow rate A2 and the flow rate A4 in order to adjust the measurement range according to the sample gas concentration. The flow rate A5 can also be changed according to a change in the flow rate A1. Furthermore, when the flow path opening/closing section 34 is controlled to set the second flow path L2 to the closed state, the flow rate A5 becomes zero and the sample gas is not introduced into the component analyzing section 300. Accordingly, the bypass flow rate control section 50 may perform control to compensate for these flow rate changes such that the sum of the flow rates A1, A5, and A6 always remains constant, in order to keep the necessary flow rate of the sample gas constant for the entire particle analyzing apparatus 100.

The bypass flow rate control section 50 may acquire information concerning the flow rate A2 of the dilution gas, the flow rate A4 of the exhaust gas, the flow rate A5 of the sample gas in the sample gas flow rate control section 32, and the open/closed state of the flow path opening/closing section 34 via the processing section 400, and control the sum of the flow rates A1, A5, and A6 to always be a constant value based on this information.

An orifice is preferably used as the sample gas flow rate control section 32, and control sections that include a drive source such as a mass flow controller or flow meter with a needle valve are preferably used as the dilution gas flow rate control section 24, the exhaust gas flow rate control section 40, and the bypass flow rate control section 50. The pipe between the sample gas source 10 and the particle measuring section 200 and the pipe between the sample gas source 10 and the component analyzing section 300 are flow paths through which the microparticles serving as the measurement target pass. Accordingly, when a mass flow controller, a flow meter with a needle valve, and the like are arranged in these flow paths, loss of microparticles is believed to occur. In this example, it is possible to reduce the loss of microparticles serving as the measurement targets, by adopting an orifice, which causes less loss of microparticles than a mass flow controller or flow meter with a needle valve, as the sample gas flow rate control section 32 arranged in the pipe between the sample gas source 10 and the component analyzing section 300.

There is no need to consider microparticle loss in the dilution gas flow rate control section 24, the exhaust gas flow rate control section 40, and the bypass flow rate control section 50 since the microparticles serving as the measurement target do not pass therethrough or pass therethrough after being measured, and so a mass flow controller or flow meter with a needle valve having a variable flow rate may be adopted here.

The processing section 400 may be a computer that processes various types of data and signals and performs various types of control. As shown by the dashed line in FIG. 1, the processing section 400 may be connected in communication with each component of the dilution gas flow rate control section 24, the exhaust gas flow rate control section 40, the particle measuring section 200, the pressure measuring section 33, the flow path opening/closing section 34, the bypass flow rate control section 50, and the component analyzing section 300. The processing section 400 may read the actual values of the flow rates from the dilution gas flow rate control section 24, the exhaust gas flow rate control section 40, and the bypass flow rate control section 50.

As seen in this example, when an orifice is used for the sample gas flow rate control section 32, the processing section 400 cannot electrically connect to the orifice itself. Accordingly, the processing section 400 may acquire a pressure value read by the pressure measuring section 33 arranged immediately after the sample gas flow rate control section 32 and calculate the flow rate A5 from the pressure value. If the pressure value has already been converted into the flow rate A5 by the pressure measuring section 33, the processing section 400 may acquire the flow rate A5 from the pressure measuring section 33.

The processing section 400 may transmit commands concerning the flow rate setting values to the dilution gas flow rate control section 24, the exhaust gas flow rate control section 40, and the bypass flow rate control section 50. The processing section 400 may transmit commands concerning the time of the open state of the flow path opening/closing section 34. The processing section 400 may calculate the open state time, i.e. the introduction time. A first external transmitting section 242 enabling communication is connected between the processing section 400 and the particle measuring section 200. A second external transmitting section 362 enabling communication is connected between the processing section 400 and the component analyzing section 300. The first external transmitting section 242 and the second external transmitting section 362 are transmission media, such as transmission cables. The processing section 400 is described in detail further below.

Figure 2:
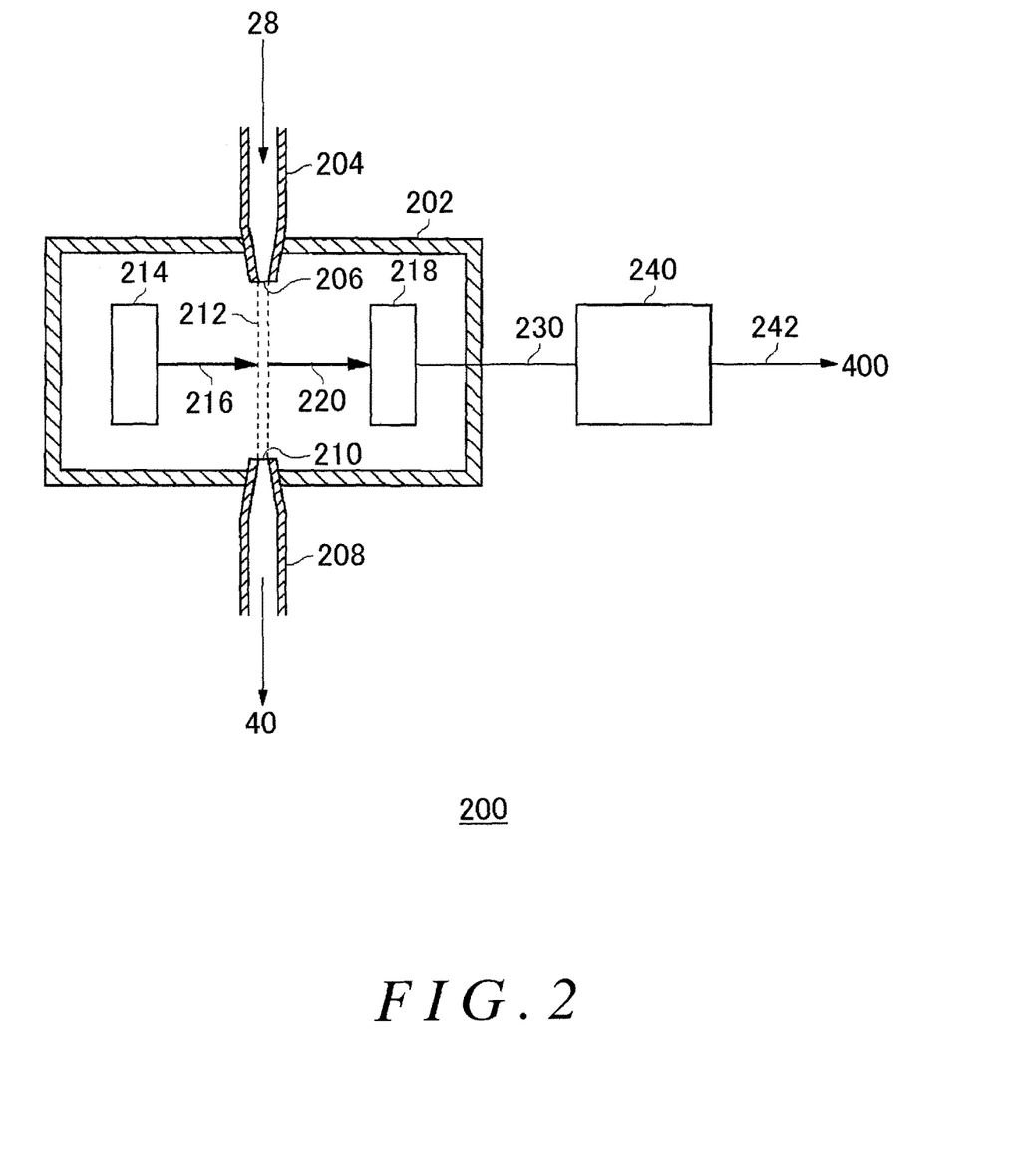
FIG. 2 is a schematic view of a configuration of an exemplary particle measuring section 200.

FIG. 2 is a schematic view of a configuration of an exemplary particle measuring section 200. The particle measuring section 200 includes a light-blocking container 202, an emission nozzle 204, a recycling nozzle 208, a laser irradiation section 214, a light receiving section 218, and a first signal processing section 240. The light-blocking container 202 may be a container surrounded by walls. The light-blocking container 202 provides a region that is shielded from outside light. The emission nozzle 204 is arranged penetrating through a portion of a wall of the light-blocking container 202. An emission opening 206 that emits gas is provided in the tip of the emission nozzle 204.

The emission nozzle 204 emits the diluted sample gas, which is introduced from the merging point 28 through the first flow path L1, from the emission opening 206. The recycling nozzle 208 is arranged penetrating through a portion of a wall of the light-blocking container 202 at a position opposite the emission nozzle 204. A recycling opening 210 that sucks in and recycles the sample gas that has been diluted is provide in the tip of the recycling nozzle 208. The recycling opening 210 of the recycling nozzle 208 is arranged opposite the emission opening 206 of the emission nozzle 204. The other end of the recycling nozzle 208 is connected to the exhaust gas flow rate control section 40 via the exhaust gas flow path L4.

The emission nozzle 204 and the recycling nozzle 208 are not limited to the examples shown in FIG. 2. The emission nozzle 204 and the recycling nozzle 208 may each have a two-layer nozzle structure. The emission nozzle 204 may form the sample gas into a beam by discharging the sample gas that includes the particles to be measured and wrapping the outside with clean sheath air. In this case, the recycling nozzle 208 may separate and recycle the sample gas and the sheath air.

The laser irradiation section 214 and the light receiving section 218 are provided inside the light-blocking container 202. The laser irradiation section 214 radiates laser light 216 across a predetermined distance toward the particle measuring region 212 between the emission nozzle 204 and the recycling nozzle 208. The light receiving section 218 receives scattered light 220 caused by the laser light 216 colliding with the particles that are the measurement target. The light receiving section 218 outputs an electrical signal according to the received optical intensity of the scattered light 220. The light receiving section 218 may include a photoelectric converter element that converts the received scattered light 220 into a pulsed electrical signal.

The first signal processing section 240 may be a received optical signal processing circuit. For example, the first signal processing section 240 is a processor such as a microcomputer. The first signal processing section 240 receives the electrical signal from the light receiving section 218 via the first signal transmitting section 230. The first signal processing section 240 performs a calculation based on the received electrical signal.

Specifically, the first signal processing section 240 may calculate the size of the particles based on the height of the pulses of the electrical signal input from the light receiving section 218. The first signal processing section 240 may calculate the number of particles based on the number of pulses in the electrical signal. The first signal processing section 240 may calculate the concentration of particles, which is the number of particles per unit volume, based on the number of particles that have been counted. If measuring the size and number of the particles, there are cases where the particle measuring section 200 measures the particle diameter distribution, which is a distribution of a number of particles of each size. The result of the calculation performed by the first signal processing section 240 is output to the processing section 400 via the first external transmitting section 242.

The light receiving section 218 may include a plurality of photoelectric converter elements arranged according to a plurality of scattering angles. In this case, the first signal processing section 240 acquires the intensity distribution of the scattered light 220 for each scattering angle, based on the electrical signals from each photoelectric converter element. Since the scattering angle of the scattered light 220 changes according to the particle size, it is possible to detect the particle diameter distribution from the intensity distribution for each scattering angle. An apparatus configured as disclosed in Japanese Patent Application Publication No. S61-14543 or Japanese Patent Application Publication No. 2012-189483, for example, can be used as the particle measuring section 200 that enables the basic configuration and basic operations described above.

Figure 3:
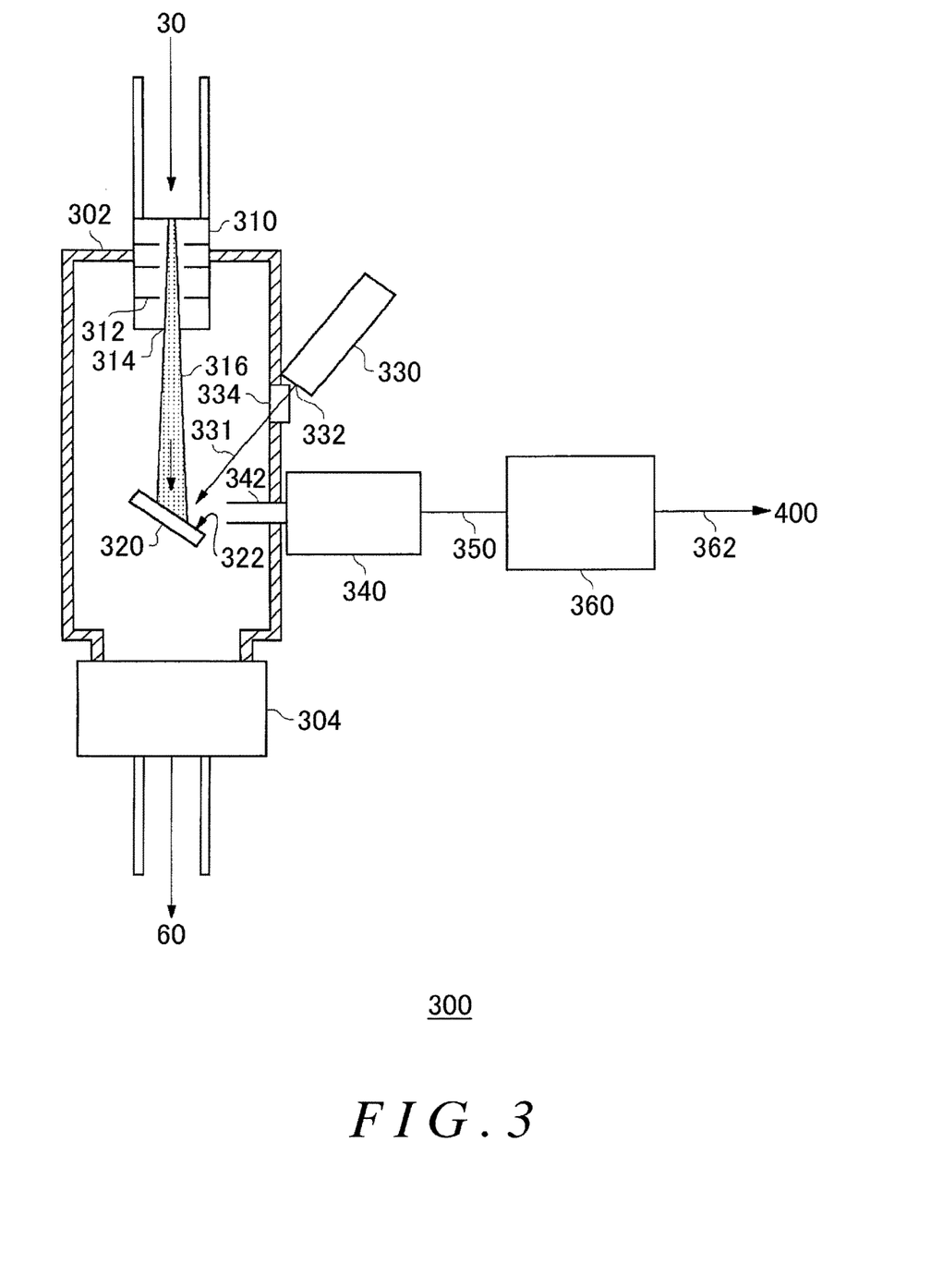
FIG. 3 shows a schematic configuration of an exemplary component analyzing section 300.

FIG. 3 shows a schematic configuration of an exemplary component analyzing section 300. The component analyzing section 300 includes a depressurized container 302, an exhaust section 304, a particle beam generating section 310, and a trap 320. The depressurized container 302 may be a depressurized chamber for providing a region that is depressurized relative to the outside. The exhaust section 304 is a vacuum pump for maintaining the depressurized state in the depressurized container 302.

The particle beam generating section 310 emits a particle beam 316 formed of the microparticles in the sample gas. The particle beam generating section 310 is an aerodynamic lens, for example. The particle beam generating section 310 is provided in a portion of a wall of the depressurized container 302. The particle beam generating section 310 penetrates through the wall of the depressurized container 302 while maintaining the air-tight state in the depressurized container 302. The particle beam generating section 310 may include a plurality of orifices 312 that have a plurality of diaphragm structures established inside a tube-shaped structure. A particle beam emission opening 314 is provided in one end of the particle beam generating section 310. The other end of the particle beam generating section 310 is connected to the second adjusting section 30.

In the present invention, the term "particle beam 316 formed of the microparticles in the sample gas" refers to the particle beam 316 formed of particles that have been compressed into a beam shape, such that each particle has the same flight and movement characteristics in the sample gas, from the sample gas in which the particles are floating freely by using the aerodynamic characteristics of particles structured as a solid or liquid. The sample gas flows into the particle beam generating section 310 due to the pressure difference between the inside and outside of the depressurized container 302. When the sample gas passes out of the inside of the particle beam generating section 310, the gas acting as a medium expands while moving, and therefore the linear motion is impeded by the orifices 312.

On the other hand, particles structured as a solid or liquid have a stronger linear progression characteristic than gas particles, and therefore the motion of particles that have passed through the first-stage orifice 312 are not significantly impeded by the second-stage and following orifices 312. Accordingly, the particles pass through the particle beam emission opening 314 while being kept in the beam shape, and are emitted as the particle beam 316 formed of particles to the outside of the depressurized atmosphere.

The trap 320 traps the particles contained in the particle beam 316. The trap 320 includes a trap surface 322 that is irradiated by the particle beam 316. The trap 320 has a mesh structure spanning at least from the trap surface 322 to a portion with a predetermined thickness. The void area ratio of the trap 320 having the mesh structure is in a range of greater than or equal to 80% and less than or equal to 99% when projecting from the trap surface 322 side. The trap 320 is arranged at a position to which the particle beam 316 is emitted. In the present embodiment, the trap 320 is arranged at a position where the particle beam 316 emitted from the particle beam emission opening 314 of the particle beam generating section 310 arrives after travelling a predetermined distance within the depressurized container 302.

The gas phase component inside the depressurized container 302 decreases due to the depressurized atmosphere, and therefore the scattering of the particles caused by the air flow occurring from the collisions with the trap 320 is restricted. The particles in the particle beam 316 lose kinetic energy while being trapped in the void of the trap 320. The trap 320 may be arranged such that the trap surface 322 is inclined and opposite to the particle beam emission opening 314 of the particle beam generating section 310. In this way, the chance of particles bouncing off the trap 320 and not being trapped is reduced, and the particles can be more efficiently trapped by the particle beam 316.

The component analyzing section 300 further includes an energy beam emitting section 330, an analyzer 340, and a second signal processing section 360. The energy beam emitting section 330 radiates an energy beam 331 toward the trap 320 and causes vaporization, sublimation, or a reaction with the particles trapped in the trap 320, thereby creating a desorbed component. The energy beam 331 arrives at the trap 320 in the depressurized container 302 through the translucent window 334 provided in a portion of a wall of the depressurized container 302. The energy beam 331 irradiates a predetermined region of the trap 320.

The energy beam 331 is not particularly limited, and may be anything that causes vaporization, sublimation, or a reaction with the particles trapped in the trap 320 to generate the desorbed component suitable for component analysis of the particles. For example, the energy beam 331 is an energy ray supplied by an infrared laser supplying device, a visible laser supplying device, an ultraviolet laser supplying device, an X-ray supplying device, or an ion beam supplying device.

The trap surface 322 of the trap 320 may be arranged somewhat inclined to and opposite the emission opening 332 of the energy beam emitting section 330. In this way, the energy beam 331 is incident at an incline with respect to a reference direction that is perpendicular to the trap surface 322. Accordingly, it becomes easy for the energy beam 331 to reach the particles trapped in the trap 320, and the particles trapped in the trap 320 can be more efficiently vaporized, sublimated, or caused to react in order to create a desorbed component.

The analyzer 340 measures the amount of each component in the particles by analyzing the desorbed component. The analyzer 340 may be a spectroscopic analyzer or mass spectrometer. The analyzer 340 outputs an analysis signal corresponding to the analyzed intensity. One end of the recycling tube section 342 is connected to the introduction opening of the analyzer 340. The other end of the recycling tube section 342 penetrates through a wall of the depressurized container 302 while maintaining the air-tight state of the depressurized container 302. The desorbed component is recycled via the recycling tube section 342 an introduced into the analyzer 340.

The second signal processing section 360 may be a processing circuit that processes the analytic signal resulting from the mass spectrometry measurement. For example, the second signal processing section 260 is a processor. The second signal processing section 360 receives the electrical signal from the analyzer 340 via the second signal transmitting section 350. The second signal transmitting section 350 transmits the analytic signal from the analyzer 340 as an electrical signal. The second signal processing section 360 calculates the components of the particles and the amount of each component based on the analytic signal received as an electrical signal. The calculation of the components of the particles and the amount of each component based on the analytic signal can be realized using conventional mass spectrometry and the like, and therefore a detailed description is omitted.

The results obtained from the calculation by the second signal processing section 360 may be output to the processing section 400 via the second external transmitting section 362. An apparatus configured as disclosed in International Publication WO 2011/114587, for example, can be used as the component analyzing section 300 that enables the basic configuration and basic operations described above.

With the component analyzing section 300, the particles in the aerosol sample gas are collected in a focused manner in a predetermined region and then irradiated with the energy beam 331 to create the desorbed component that is to be analyzed, and therefore it is possible to analyze the components of the particles and the amount of each component with high efficiency and high sensitivity. Furthermore, with the particle analyzing apparatus 100 of this example, it is possible to measure the amount of each component with the component analyzing section 300 while measuring the number, size, and concentration of the particles with the particle measuring section 200, and therefore it is possible to provide a composite particle analyzing apparatus that is suitable for analyzing measurement target particles in various ways.

Figure 4:
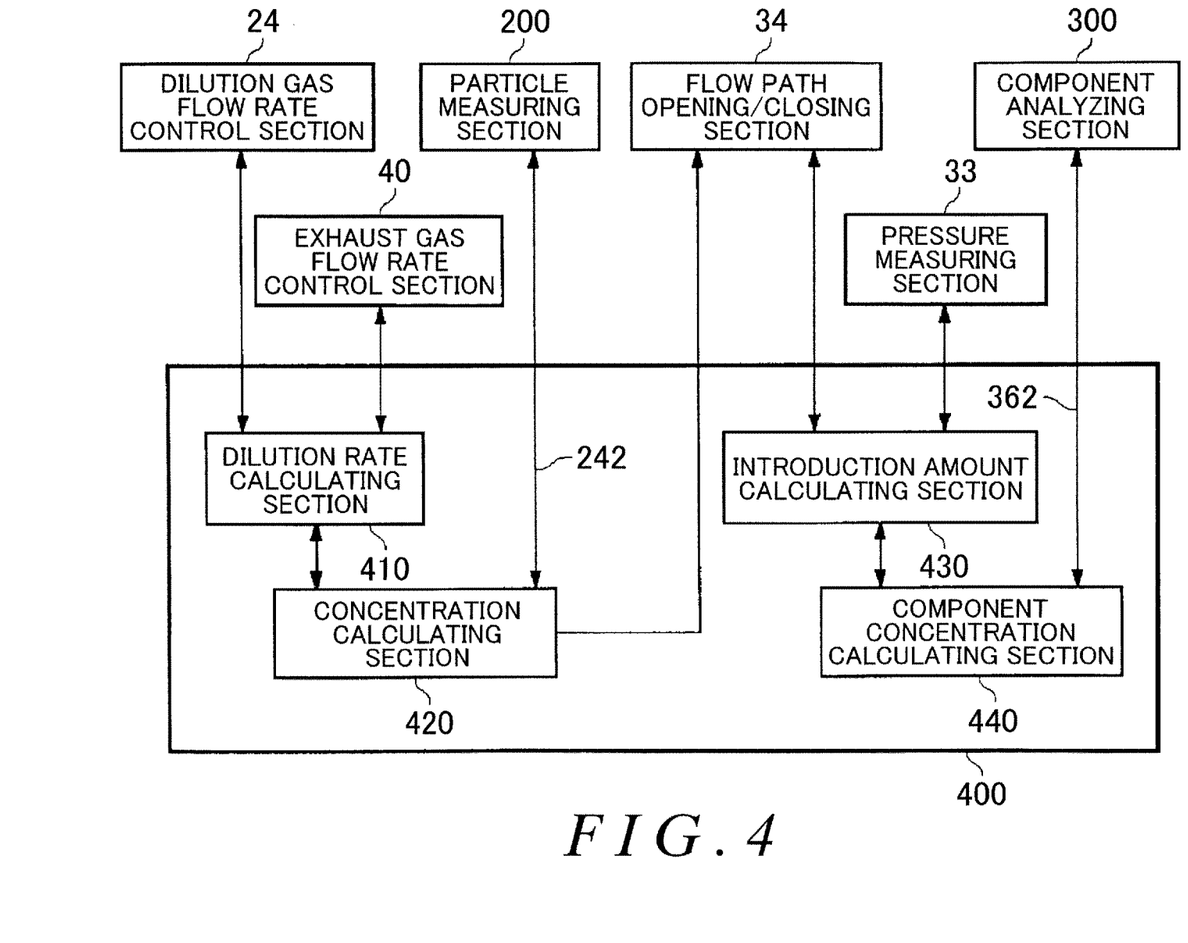
FIG. 4 shows an exemplary processing section 400.

FIG. 4 shows an exemplary processing section 400 in the particle analyzing apparatus 100. The processing section 400 in this example includes a dilution rate calculating section 410, a concentration calculating section 420, an introduction amount calculating section 430, and a component concentration calculating section 440. The dilution rate calculating section 410 and the concentration calculating section 420 calculate the dilution rate and the concentration for the particle analyzing section 200. The dilution rate calculating section 410 calculates the dilution rate based on the flow rate A2 of the dilution gas for the dilution gas flow rate control section 24 and the flow rate A4 of the exhaust gas for the exhaust gas flow rate control section 40. The concentration calculating section 420 calculates the concentration of the particles in the original sample gas before dilution, based on the measurement results of the particle measuring section 200 and the calculated dilution rate.

The introduction amount calculating section 430 and the component concentration calculating section 440 perform control and various calculations relating to the component analyzing section 300. The introduction amount calculating section 430 calculates the introduction amount of the sample gas into the component analyzing section 300 based on the flow rate A5 per unit time of the sample gas for the sample gas flow rate control section 32 and the introduction time T1 of the sample gas into the component analyzing section 300. The introduction time T1 is adjusted by the flow path opening/closing section 34. The component concentration calculating section 440 calculates the concentration of each component based on the measurement results from the component analyzing section 300 and the calculated introduction amount.

The processing section 400 is not limited to receiving the measurement results and calculation results from each component, and may also transmit control information such as various commands to each component. For example, the processing section 400 designates desired flow rate setting values for the dilution gas flow rate control section 24 and the exhaust gas flow rate control section 40.

The introduction amount calculating section 430 and the component concentration calculating section 440 may provide instructions to the flow path opening/closing section 34 of the second adjusting section 30 such that the calculated introduction amount is within a predetermined range. Based on these instructions, the second adjusting section 30 may adjust the open state time of the flow path opening/closing section 34 to control the sample gas introduction amount to be within the prescribed range. The processing section 400 described above may be a single computer or may be a plurality of computers. The processing section 400 need not be arranged in a single casing, and may be divided up and provided in one or both of the particle measuring section 200 and the component analyzing section 300.

The particle analyzing apparatus 100 in this example having the configuration described above performs the following processes. In FIG. 1, the flow rate A2 of the dilution gas supplied from the dilution gas source 22 may be controlled by the dilution gas flow rate control section 24 to be the flow rate setting value. The flow rate setting value may be designated by the processing section 400 or may be directly input by the first adjusting section 20. On the other hand, with the flow rate from the sample gas source 10 being A1, as shown in FIG. 1, the flow rate A3 of the diluted sample gas introduced to the particle measuring section 200 becomes the sum of the flow rate A1 and the flow rate A2.

The flow rate A4 of the exhaust gas output and recycled from the particle measuring section 200 is controlled to be the flow rate setting value by the exhaust gas flow rate control section 40, and is equal to the flow rate A3. The flow rate setting value for the flow rate A4 may be designated by the processing section 400 or may be directly input. Accordingly, the aerosol sample introduced to the first particle measuring section 200 is the sample gas with a dilution obtained from a flow rate of A4/A3, i.e. a flow rate of A4/(A4−A2). The dilution rate calculating section 410 may acquire the actual measurement value of the flow rate A2 from the dilution gas flow rate control section 24, and may acquire the actual measurement value of the flow rate A4 from the exhaust gas flow rate control section 40. The dilution rate calculating section 410 calculates the dilution rate E1 by calculating A4/(A4−A2) using the acquired values of A2 and A4.

With the particle analyzing apparatus 100 in this example, it is possible to calculate the dilution rate E1 without using the equipment such as the mass flow controller for measuring the flow rate A1 from the sample gas source 10 located upstream from the particle measuring section 200. Accordingly, the configuration of the apparatus can be simplified, and it is also possible to conserve space and reduce the cost. In a case where the processing section 400 transmits instructions for the setting flow rate value of the flow rate A2 to the dilution gas flow rate control section 24 and transmits instructions for the setting flow rate value for the flow rate A4 to the exhaust gas flow rate control section 40, the dilution rate calculating section 410 may calculate the dilution rate using the flow rate setting values instead of the actual measurement values of the flow rates.

The particle measuring section 200 may measure the concentration of particles in the sample gas. With the measured value of the particle concentration being S1, the measurement value S1 of the concentration is multiplied by a dilution rate E1. Accordingly, the particle concentration in the original sample gas that has not yet been diluted is a value obtained by multiplying the measurement value S1 of the concentration by the inverse of the dilution rate E1. The concentration calculating section 420 of the processing section 400 may acquire the measurement value S1 from the first signal processing section 240 of the particle measuring section 200 via the first external transmitting section 242. The concentration calculating section 420 calculates the concentration of the particles in the original sample gas that has not been diluted by multiplying the acquired measurement value S1 by the inverse of the dilution rate E1.

In the measurement performed by the particle measuring section 200, when the particle concentration in the sample gas is high and a plurality of particles overlap in the optical path of the laser light 216, there are cases where it is difficult to perform an accurate measurement. However, with the particle analyzing apparatus 100 of this example, measurement is performed after a sample gas with a high particle concentration is diluted, and the actual concentration can be calculated by multiplying the resulting value by the dilution coefficient, and therefore the measurement range can be increased.

The second adjusting section 30 is provided upstream in the component analyzing section 300. The second adjusting section 30 includes the sample gas flow rate control section 32 and the flow path opening/closing section 34. With the flow rate A5 indicating the flow rate controlled by the sample gas flow rate control section 32, i.e. the flow rate of the sample gas introduced to the component analyzing section 300, the introduction amount of the sample gas to the component analyzing section 300 can be calculated as the product of the flow rate 5A and the introduction time T1, which is the open state time of the flow path opening/closing section 34.

The introduction amount calculating section 430 of the processing section 400 may acquire the flow rate A5 calculated from the measurement value of the pressure measuring section 33. The introduction amount calculating section 430 may acquire the open state time T1 from the flow path opening/closing section 34. The introduction amount calculating section 430 calculates the introduction amount by calculating the product A5×T1 using the acquired values A5 and T1. If the processing section 400 is transmitting commands concerning the open state time of the flow path to the flow path opening/closing section 34, the introduction amount calculating section 430 may calculate the introduction amount using the acquired flow rate A5 and the instructed open state time, while tracking the open and closing operation of the flow path opening/closing section 34.

The component analyzing section 300 may measure the mass of each component of the particles in the sample gas. With S2 representing the measurement value of the mass of each component, the mass concertation of each component is the value S2/(A5×T1) obtained by dividing the measurement value S2 by (A5×T1). The component concentration calculating section 440 may acquire the measurement value S2 from the second signal processing section 360 of the component analyzing section 300, via the second external transmitting section 362. The component concentration calculating section 440 calculates the mass concentration of each component in the sample gas by dividing the acquired measurement value S2 by the introduction amount (A5×T1).

If the measurement made by the component analyzing section 300 includes trapping the majority of particles of the particle beam 316 in the trap 320 and creating a desorbed component by irradiating the majority of the trapped particles with the energy beam 331, the mass concentration of each component can be calculated according to S2/(A5×T1).

On the other hand, if the trap 320 has already trapped a predetermined amount of particles, it is impossible to trap enough particles even if more particles are introduced. Accordingly, if an amount of particles beyond what can be trapped by the trap 320 are introduced, it is difficult to accurately measure the concentration of each component.

Accordingly, the component analyzing section 300 controls the introduction amount such that the amount of particles introduced to the component analyzing section 300 does not exceed a predetermined range. By controlling the open state time T1 of the flow path opening/closing section 34 to be short enough that the particle introduction amount is within the predetermined range, it is possible to increase the measurement range.

If the concentration of particles in the sample gas is relatively high, even if the introduction amount (A5×T1) of the sample gas is relatively low, there are cases where the actual introduction amount of particles contained in the sample gas is high. When the number or concentration of particles measured by the particle measuring section 200 is higher, it can be determined that the actual introduction amount of particles is high even if the same sample gas introduction amount of (A5×T1) is used. Accordingly, when the number or concentration of particles measured by the particle measuring section 200 that can be measured in a relatively short time is higher, the introduction time T1 of the sample gas into the component analyzing section 300 may be controlled to be shorter. Specifically, the processing section 400 acquires the detection results of the particle measuring section 200 and, based on the acquired detection results, may transmit commands concerning the open state time of the flow path opening/closing section 34.

With the particle analyzing apparatus 100 of this example, by mixing together the sample gas and the gas such as clean dilution air that does not contain particles and introducing this resulting gas into the particle measuring section 200, it is possible to increase the measurement range of the particle measuring section 200. Accordingly, the particle analyzing apparatus 100 of this example can be used for measurement at any location where there is a high concentration of particles to be measured. The particle analyzing apparatus 100 can directly measure particles that have a high concentration emitted from an exhaust source. On the other hand, by reducing the introduction time during which the sample gas need be introduced into the component analyzing section 300 compared to the conventional technology, it is possible to increase the measurement range of the component analyzing section 300.

With the particle analyzing apparatus 100 of this example, in a composite analyzing apparatus used for various types of analyses of target particles, it is possible to increase the measurement range of each of the particle measuring section 200 and the component analyzing section 300 included therein independently by a desired amount. Since a wide measurement range can be adopted for both the particle measuring section 200 and the component analyzing section 300, it is possible to increase the measurement range without reducing the measurement capability.

Figure 5:
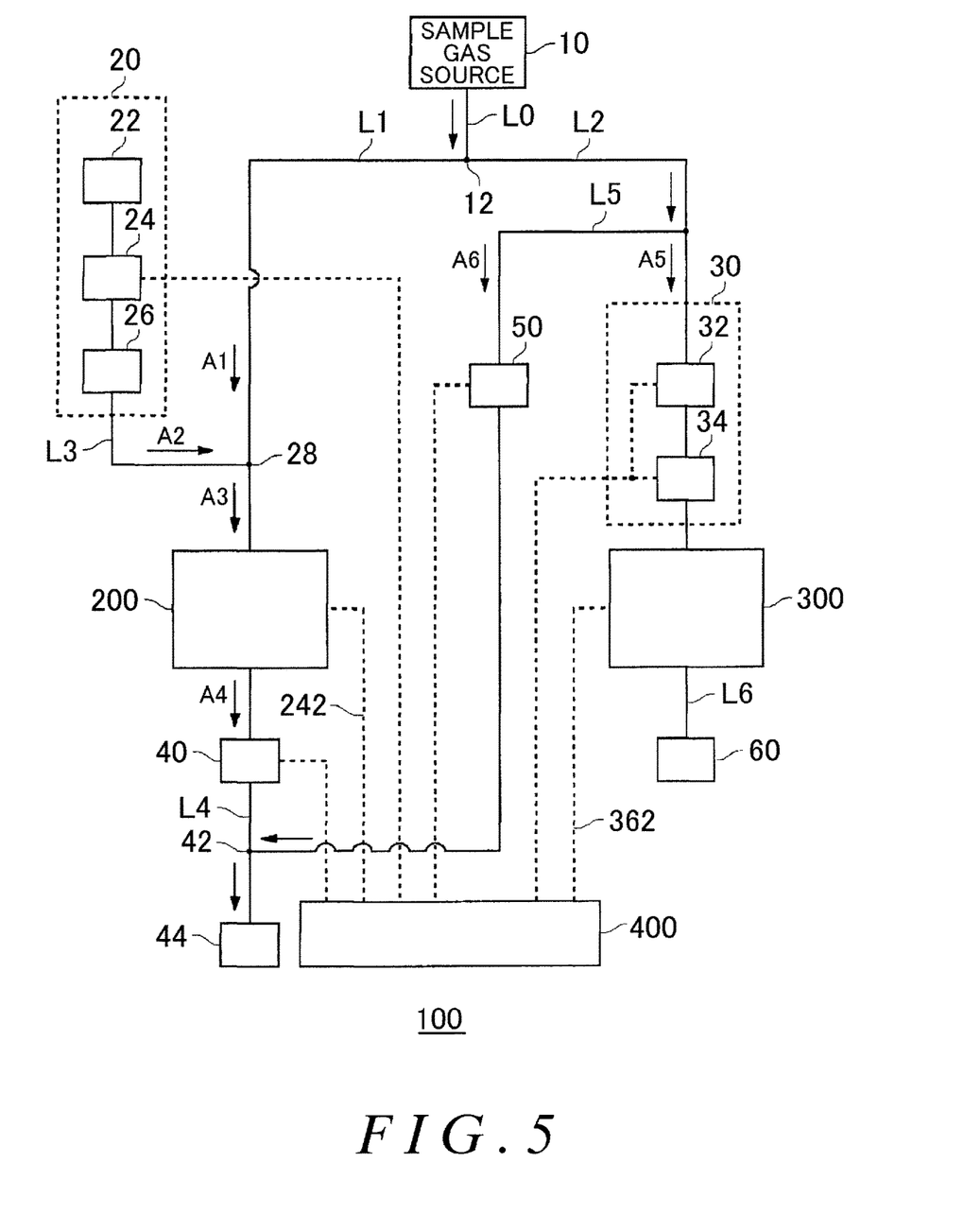
FIG. 5 shows another exemplary configuration of an overall particle analyzing apparatus 100.
Figure 6:
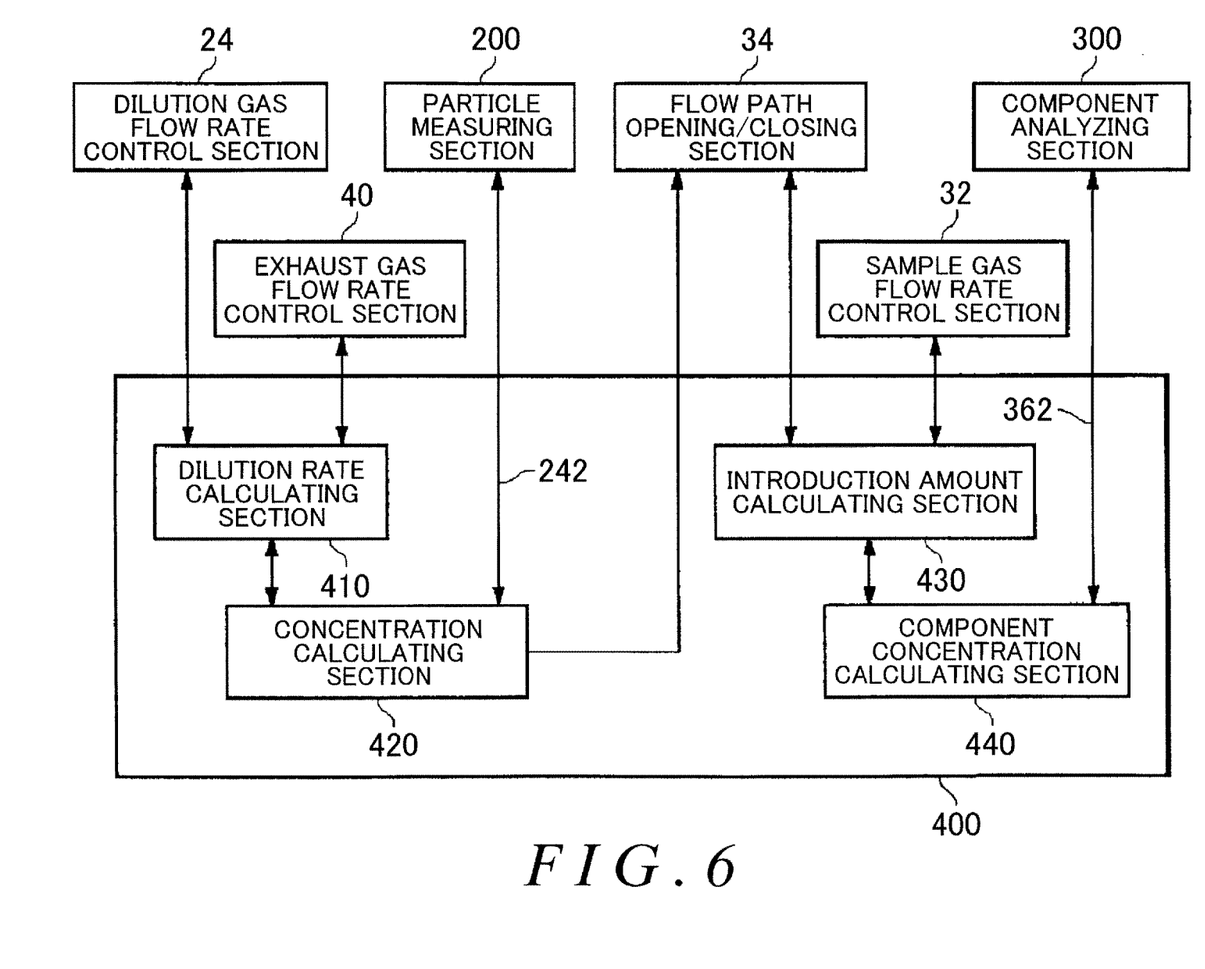
FIG. 6 shows another example of a processing section 400.

In the above description, orifices without a drive source are used as the sample gas flow rate control section 32 and the pressure measuring section 33 is provided immediately after the orifices, but the present invention is not limited to this example. FIG. 5 shows another exemplary configuration of an overall particle analyzing apparatus 100. FIG. 6 shows another example of a processing section 400. If microparticle loss is not a problem, a mass flow controller or flow meter with a needle valve may be used as the sample gas flow rate control section 32, and the pressure measuring section 33 may be omitted as shown in FIG. 5.

As shown by the dashed lines in FIG. 5, the processing section 400 may be connected in a communicable manner to the dilution gas flow rate control section 24, the exhaust gas flow rate control section 40, the particle measuring section 200, the sample gas flow rate control section 32, the flow path opening/closing section 34, the bypass flow rate control section 50, and the component analyzing section 300. The processing section 400 may read the actual measurement values of the flow rates from the dilution gas flow rate control section 24, the exhaust gas flow rate control section 40, the sample gas flow rate control section 32, and the bypass flow rate control section 50. The processing section 400 may transmit commands concerning the flow rate setting values to the dilution gas flow rate control section 24, the exhaust gas flow rate control section 40, and the bypass flow rate control section 50.

As shown in FIG. 6, the introduction amount calculating section 430 of the processing section 400 may acquire the actual measurement value of the flow rate A5 from the sample gas flow rate control section 32. The introduction amount calculating section 430 calculates the introduction amount by calculating (A5×T1) using the acquired values of A5 and T1. If the processing section 400 transmits commands concerning the flow rate setting value for the flow rate A5 to the sample gas flow rate control section 32 and transmits commands concerning the open state time of the flow path to the flow path opening/closing section 34, the introduction amount calculating section 430 may calculate the introduction amount using the open state time according to the commands and the flow rate setting value for the flow rate A5, according to the tracking abilities of the flow rate and open/close operation of the sample gas flow rate control section 32 and the flow path opening/closing section 34.

In the examples shown in FIGS. 5 and 6 as well, the bypass flow rate control section 50 may perform control such that the necessary flow rate of the sample gas introduced from the sample gas source 10 to the entire particle analyzing apparatus 100 is within a predetermined range. For example, in order to maintain the necessary flow rate of the sample gas for the entire particle analyzing apparatus 100, the bypass flow rate control section 50 may control the sum of the flow rates A1, A5, and A6 to always be a constant amount. Specifically, the processing section 400 may transmit commands concerning the flow rate setting values to the bypass flow rate control section 50, according to the open/closed state of the flow path opening/closing section 34 and the flow rates for the dilution gas flow rate control section 24, the exhaust gas flow rate control section 40, and the sample gas flow rate control section 32. The bypass flow rate control section 50 may control the flow rates such that the sum of the flow rates A1, A5, and A6 remains constant, based on the commands concerning the flow rate setting values.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

LIST OF REFERENCE NUMERALS

10: sample gas source, 12: branching point, 20: first adjusting section, 22: dilution gas source, 24: dilution gas flow rate control section, 26: cleaning section, 28: merging point, 30: second adjusting section, 32: sample gas flow rate control section, 33: pressure measuring section, 34: flow path opening/closing section, 40: exhaust gas flow rate control section, 42: bypass merging point, 44: first vacuum section, 50: bypass flow rate control section, 60: second vacuum section, 100: particle analyzing apparatus, 200: particle measuring section, 202: light-blocking container, 204: emission nozzle, 206: emission opening, 208: recycling nozzle, 210: recycling opening, 212: particle measuring region, 214: laser irradiation section, 216: laser light, 218: light receiving section, 220: scattered light, 230: first signal transmitting section, 240: first signal processing section, 242: first external transmitting section, 300: component analyzing section, 302: depressurized container, 304: exhaust section, 310: particle beam generating section, 312: orifice, 314: particle beam emission opening, 316: particle beam, 320: trap, 322: trap surface, 330: energy beam emitting section, 331: energy beam, 332: emission opening, 334: translucent window, 340: analyzer, 342: recycling tube section, 350: second signal transmitting section, 360: second signal processing section, 362: second external transmitting section, 400: processing section, 410: dilution rate calculating section, 420: concentration calculating section, 430: introduction amount calculating section, 440: component concentration calculating section

What is claimed is:

1. A particle analyzing apparatus comprising:
   a particle measuring section that measures a number or concentration of particles in a sample gas, based on laser light that is scattered by the particles in the sample gas;
   a component analyzing section that measures an amount of each component of the particles in the sample gas;
   a flow path that has one end thereof connected to a sample gas source and, at a branching point at the other end side, branches into a first flow path that introduces the sample gas to the particle measuring section and a second flow path that introduces the sample gas to the component analyzing section;
   a first adjusting section that is provided in the first flow path and dilutes the sample gas with a dilution gas and introduces the diluted sample gas to the particle measuring section to adjust a measurement range of the particle measuring section; and
   a second adjusting section that is provided in the second flow path and adjusts an introduction time during which the sample gas is introduced to the component analyzing section.

2. The particle analyzing apparatus according to claim 1, wherein the first adjusting section includes:
   a dilution gas flow path that has one end thereof connected to a dilution gas source and another end thereof connected to the first flow path; and
   a dilution gas flow rate control section that is provided in the dilution gas flow path and controls a flow rate of the dilution gas introduced to the first flow path.

3. The particle analyzing apparatus according to claim 2, comprising:
   an exhaust gas flow rate control section that controls a flow rate of an exhaust gas emitted from the particle measuring section.

4. The particle analyzing apparatus according to claim 3, comprising:
   a dilution rate calculating section that calculates a dilution rate based on the flow rate of the dilution gas in the dilution gas flow rate control section and the flow rate of the exhaust gas in the exhaust gas flow rate control section; and
   a concentration calculating section that calculates a concentration of particles in the sample gas that has not been diluted, based on the dilution rate and a measurement result of the particle measuring section.

5. The particle analyzing apparatus according to claim 1, wherein the second adjusting section includes:
   a sample gas flow rate control section that is arranged in the second flow path and controls a flow rate of the sample gas; and
   a flow path opening/closing section that is arranged in the second flow path and adjusts an introduction time during which the sample gas is introduced into the component analyzing section by switching between an open state and a closed state.

6. The particle analyzing apparatus according to claim 5, comprising:
   an introduction amount calculating section that calculates an introduction amount of the sample gas into the component analyzing section based on the flow rate of the sample gas in the sample gas flow rate control section and the introduction time during which the sample gas is introduced into the component analyzing section as adjusted by the flow path opening/closing section, wherein
   the second adjusting section controls an introduction rate of the sample gas to be within a predetermined range by adjusting a time of the open state of the flow path opening/closing section.

7. The particle analyzing apparatus according to claim 1, wherein the component analyzing section includes:
   a particle beam generating section that emits a particle beam formed by particles in the sample gas;
   a trap that is arranged at a position at which the particle beam is emitted and traps the particles in the particle beam;
   an energy beam emitting section that irradiates the trap with an energy beam to create a desorbed component by vaporizing, sublimating, or causing a reaction with the particles trapped in the trap; and
   an analyzer that measures an amount of each component of the particles by analyzing the desorbed component.

8. The particle analyzing apparatus according to claim 1, comprising:
   a bypass flow path that branches from the second flow path;
   a bypass flow rate control section that is provided in the bypass flow path and controls a flow rate of the sample gas flowing through the bypass flow path such that a necessary flow rate of the sample gas introduced into the entire particle analyzing apparatus from the sample gas source is within a predetermined range; and
   an exhaust gas flow path through which flows exhaust gas emitted from the particle measuring section, wherein
   the bypass flow path is connected to the exhaust gas flow path.

9. The particle analyzing apparatus according to claim 1, wherein
   the introduction time of the sample gas is shorter when the number or concentration of the particles measured by the particle measuring section is higher.

* * * * *